United States Patent
Ahmed et al.

(10) Patent No.: US 10,653,666 B1
(45) Date of Patent: May 19, 2020

(54) CARDIOPROTECTIVE NANO-PHARMACEUTICAL FORMULATION

(71) Applicant: King Abdulaziz University, Jeddah (SA)

(72) Inventors: Osama A. A. Ahmed, Jeddah (SA); Usama A. Fahmy, Jeddah (SA); Noura A. Hassan, Jeddah (SA); Ahmad S. Azhar, Jeddah (SA); Mahmoud M. El-Mas, Jeddah (SA); Hany El-Bassossy, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/741,826

(22) Filed: Jan. 14, 2020

(51) Int. Cl.
| | | |
|---|---|---|
| *A61K 36/00* | (2006.01) | |
| *A61K 31/355* | (2006.01) | |
| *A61P 9/04* | (2006.01) | |
| *A61K 47/34* | (2017.01) | |
| *A61K 36/42* | (2006.01) | |

(52) U.S. Cl.
CPC ............ *A61K 31/355* (2013.01); *A61K 36/42* (2013.01); *A61K 47/34* (2013.01); *A61P 9/04* (2018.01)

(58) Field of Classification Search
CPC .................................................... A61K 36/00
See application file for complete search history.

(56) References Cited

U.S. PATENT DOCUMENTS

| | | |
|---|---|---|
| 7,683,095 B2 | 3/2010 | Guthrie et al. |
| 8,835,509 B2 | 9/2014 | Kohli et al. |

FOREIGN PATENT DOCUMENTS

| | | |
|---|---|---|
| EP | 2985276 | 2/2016 |

OTHER PUBLICATIONS

Date et al., "Self-nanoemulsifying drug delivery systems: Formulation insights, applications and advances", Nanomedicine, Dec. 2010, 5(10), 1595-1616.
Rivera et al., "Quercetin Ameliorates Metabolic Syndrome and Improves the Inflammatory Status in Obese Zucker Rats", Obesity (2008) 16, 2081-2087.
Santos et al., "Dissection of the Effects of Quercetin on Mouse Myocardium", BCPT (2017), 120, 550-559.
Tran et al., "Quercetin-containing self-nanoemulsifying drug delivery system for improving oral bioavailability", J Pharm Sci. Mar. 2014; 103(3):840-52.
Zahedi et al., "Does Quercetin Improve Cardiovascular Risk factors and Inflammatory Biomarkers in Women with Type 2 Diabetes: A Double-blind Randomized Controlled Clinical Trial", Int J Prev Med. Jul. 2013; 4(7):777-785.

*Primary Examiner* — Qiuwen Mi
(74) *Attorney, Agent, or Firm* — W & C IP

(57) ABSTRACT

A nano-pharmaceutical formulation, comprising pumpkin seed oil; D-α-tocopheryl polyethylene glycol succinate (TPGS); and polyethylene glycol (PEG) 200 is provided. Additional cardioprotective therapies such as quercetin may be included in the formulation. Methods of treating cardiac dysfunction by administering the formulation are also provided.

5 Claims, 4 Drawing Sheets

CARDIOPROTECTIVE NANO-PHARMACEUTICAL FORMULATION

FIELD OF THE INVENTION

The invention is generally related to a nano-pharmaceutical formulation having cardioprotective activity either alone or in combination with additional cardiovascular therapies.

BACKGROUND OF THE INVENTION

Metabolic syndrome (MetS), also referred to as insulin resistance syndrome or syndrome X, is characterized by a cluster of conditions, namely: central obesity, dyslipidemia, hypertension and hyperglycemia (Alberti et al., 2005). The detrimental effect of MetS in general is its close association with the development of cardiovascular diseases (CVD) and type 2 diabetes mellitus. A major indicator of the cardiovascular complications associated with MetS is vascular damage which is translated into exaggerated contraction and attenuated dilation of the blood vessels in response to vasoconstrictors and vasodilators respectively (Bahia et al., 2006). Hypertension leading to arterial wall stiffness, as well as atherosclerosis secondary to dyslipidemia, are some of the MetS conditions which catalyze the appearance of the vascular dysfunction observed (Olijhoek et al., 2004; Oliver and Webb, 2003).

Given the detrimental effects MetS has on health, there is a growing interest in the use of natural products, specifically plant polyphenols, combined with synthetic drugs for better control of the disease (Visioli, 2011). Quercetin is a ubiquitous compound, found in many fruits and vegetables including apples, peppers and onions. Quercetin is reported to confer diverse health benefits, such as anti-inflammation, antioxidant and endothelial NO upregulation (Jagtap et al., 2009; Murakami et al., 2008; Shen et al., 2012). Consequently, quercetin is a potential compound that could be used to reduce MetS-initiated vascular damage. However, the exact mechanisms by which quercetin brings forth these advantageous actions remain unclear.

Thus, new formulations are needed for treatment of cardiovascular disorders and to enhance delivery of cardiovascular therapies.

SUMMARY

An aspect of the disclosure provides a nano-pharmaceutical formulation, comprising pumpkin seed oil, D-α-tocopheryl polyethylene glycol succinate (TPGS), and polyethylene glycol (PEG) 200. In some embodiments, the concentration of pumpkin seed oil is 20%. In some embodiments, the concentration of TPGS is 50%. In some embodiments, the concentration of PEG 200 is 30%. In some embodiments, the formulation further comprises a biologically active agent for treatment of cardiac dysfunction. In some embodiments, the biological active agent is quercetin.

Another aspect of the disclosure provides a method of treating cardiac dysfunction in a subject in need thereof, comprising administering a therapeutically effective amount of a formulation as described herein to the subject. In some embodiments, the subject suffers from metabolic syndrome.

Another aspect of the disclosure provides a method of improving or increasing the bioavailability of quercetin by providing a formulation as described herein.

Another aspect of the disclosure provides a method of improving or increasing cardioprotective activity of quercetin by providing a formulation as described herein.

DETAILED DESCRIPTION

Figure 1:
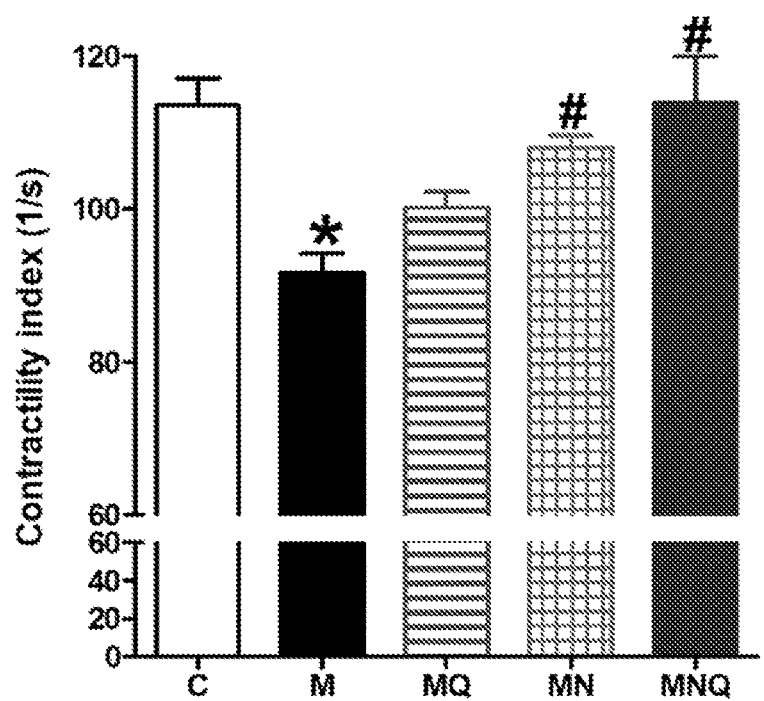
FIG. 1. Effect of oral administration of standard quercetin suspension (MQ), plain nano-pharmaceutical formulation (MN) and the quercetin loaded nano-pharmaceutical formulation (MNQ) both at 25 mg/kg/day on impaired cardiac contractility associated with metabolic syndrome (M) induced by feeding rats a high fructose (10% in drinking water), high salt (3%) diet for 12 weeks. Results are expressed as mean±SEM (n=8 for all groups). * $p<0.05$ when compared to the corresponding control values, # $p<0.05$ when compared to the corresponding MetS values using one-way ANOVA followed by Dunnet's post-hoc test.

Embodiments of the disclosure provide nano-pharmaceutical formulations that provide a cardioprotective effect when administered without any additional therapeutic active agent. The formulations may also used to form a self-nanoemulsifying drug delivery system (SNEDDS) for the enhanced delivery and improved bioavailability of a therapeutic active agent such as quercetin. As shown in the Example, the combination of the nano-pharmaceutical formulation and quercetin provides additive cardioprotective activity.

SNEDDS are homogenous anhydrous liquid mixtures comprising oil, surfactant, and a coemulsifier or solubilizer that spontaneously form oil in water nanoemulsions (e.g. about 200 nm or less in size) upon dilution with water under gentle stirring. SNEDDS may be used to improve the solubility and bioavailability of hydrophobic drugs. Nanoemulsion fabrication methods are known in the art and comprise both high-energy and low-energy emulsification methods (Date et al., Nanomedicine (2010) 5(10), 1595-1616).

In an embodiment, pumpkin seed oil comprises the oily phase of the oil-in-water nanoemulsion. Oil may be extracted from pumpkin seeds according to methods known in the art, e.g. by solvent extraction or by supercritical dioxide methods. Pumpkin seed oil products are also sold commercially.

Other oils may be included in addition to or alternatively to pumkin seed oil such as black seed oil, soybean oil, coconut oil, canola oil, safflower oil, olive oil, corn oil, cottonseed oil, linseed oil, safflower oil, palm oil, peanut oil, flaxseed oil, sunflower oil, rice bran oil, sesame oil, rapeseed oil, cocoa butter, almond oil, cashew oil, hazelnut oil, macadamia oil, mongongo nut oil, pecan oil, pine nut oil, pistachio oil, sachainchi oil, walnut oil, bottle gourd oil, buffalo gourd oil, butternut squash seed oil, watermelon seed oil, acai oil, blackcurrant seed oil, borage seed oil, evening primrose oil, carob pod oil, amaranth oil, apricot oil, apricot kernel oil, apple seed oil, argan oil, artichoke oil, avocado oil, babassu oil, ben oil, borneo tallow nut oil, cape chestnut oil, cassia oil, cocoa butter, cocklebur oil, cohune oil, coriander seed oil, dika oil, grape seed oil, hemp oil, kapok seed oil, kenaf seed oil, lallemantia oil, manila oil, meadowfoam seed oil, mustard oil, nutmeg butter, okra seed oil, papaya seed oil, perilla seed oil, pequi oil, poppyseed oil, prune kernel oil, quinoa oil, ramtil oil, royle oil, tea seed oil, thistle oil, tigernut oil, tomato seed oil, wheat germ oil, radish oil, salicornia oil, tung oil, algae oil, copaiba oil, honge oil, jatropha oil, petroleum nut oil, WL 1349 oil, a silicone oil, and a mineral oil.

Embodiments of the disclosure provide a tocopherol or derivative thereof as a nonionic surfactant. Tocopherols are a class of methylated phenols, many of which have vitamin E activity. Tocopherols and their derivatives, such as esters for example, are widely used in vitamin supplementation and as antioxidants in the food industry and in many pharmaceutical compositions. Tocopherols are a range of natural and synthetic compounds, also known by the generic term Vitamin E. α-Tocopherol (chemical name: 2,5,7,8-tetramethyl-2-(4',8',12'-trimethyldecyl)-6-chromanole) is the most active and widely distributed in nature, and has been the most widely studied. Other members of the class include beta, gamma, and delta tocopherols. Tocopherols occur in a number of isomeric forms, the D and DL forms being the most widely available. As used herein, the term "tocopherol" includes all such natural and synthetic tocopherol or Vitamin E compounds.

Any of the forms or isomers of tocopherols and their derivatives, eg. esters may be used according to the present disclosure. Thus for example, α-tocopherol can be used as such or in the form of its esters such as α-tocopherol acetate, linoleate, nicotinate or hemi succinate-ester, many of which are available commercially.

The tocopherol derivative includes chemical derivatives of vitamin E with ester and ether linkages of various chemical moieties to polyethylene glycol of various lengths. For example, the derivative may include vitamin E tocopherol polyethylene glycol succinate (TPGS) derivatives with PEG molecular weights between about 500 and 6000 Da. In some embodiments, the vitamin E polymeric derivative is D-α-Tocopherol polyethylene glycol 1000 succinate (TPGS). In an embodiment, the tocopherol is present in the composition from about 40 wt % to about 60 wt %/volume, e.g. about 50 wt %. It should be understood that throughout the specification the term weight percent (wt %) refers to mass per unit volume, unless otherwise specified.

TPGS is a water soluble derivative of Vitamin E in which polyethylene glycol subunits are attached by a succinic acid diester at the ring hydroxyl of the vitamin E molecule. TPGS is an almost odourless waxy amphiphilic substance with a molecular weight about 1513.

The tocopherol surfactant of the disclosure may be used alone or in conjunction with other known surfactants eg. phospholipids, polysorbates, sorbitan esters of fatty acids, cetearyl glucoside or poloxamers or other stabilisers such as xanthan gum, or propylene glycol alginate. In some embodiments, the surfactant comprises polyethylene glycol (PEG) of various molecular weights, such as PEG 200. In an embodiment, the additional surfactant is present in the composition from about 20 wt % to about 40 wt %/volume, e.g. about 30 wt %.

As demonstrated in the Example, it was found that a formulation consisting of pumpkin seed oil, TPGS, and PEG 200, without any other active agent, provided a cardioprotective effect. In some embodiments, formulation is loaded with one or more additional biological active agents to enhance its delivery to a human or non-human animal subject. In some embodiments, the active agent has a solubility in water (w/v) which is 3% or less, e.g. 1% or less. In some embodiment, the active agent is suitable for treatment of cardiac dysfunction. In some embodiments, the active agent is a flavonoid such as quercetin. In some embodiments, the active agent is a diuretic, vasodilator, digoxin, inotropic agent, anti-coagulant, beta-blocker, ACE inhibitor, angiotensin II receptor blocker, or a statin.

The formulations of the disclosure are suitable for oral administration. The present disclosure also provides a method of treatment of a human or non-human animal subject by delivery of a substantially insoluble or sparingly soluble biologically active agent, said method comprising administering to said subject a formulation as described herein, with or without an additional biological active agent.

Embodiments of the disclosure also provide methods of treating cardiac dysfunction in a subject in need thereof, comprising administering a formulation as described herein to the subject. In some embodiments, the subject suffers from metabolic syndrome. Metabolic syndrome is a cluster of conditions that occur together, increasing the risk of heart disease, stroke, and type 2 diabetes. These conditions include increased blood pressure, high blood sugar, excess body fat around the waist, and abnormal cholesterol or triglyceride levels. In some embodiments, the formulation described herein is administered in an amount effective to treat or alleviate one of more of these conditions. Treating or alleviating cardiac dysfunction may include one or more of improving cardiac contractility, an increase of ejection fraction, increase in diastolic and/or systolic function, improvement in hemodynamics, reductions in arrhythmias, protection against ischemic heart diseases and improvement in heart rate variability.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the formulation or active agent is administered to the subject in a therapeutically effective amount. By a "therapeutically effective amount" is meant a sufficient amount to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

In some embodiments, the dosage level of quercetin is 20-30 mg/kg, e.g. about 25 mg/kg.

The active agent may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Embodiments of the disclosure also provide methods of preparing self-nanoemulsifying drug delivery systems. Such methods are known in the art.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLE

Summary

A quercetin loaded nano-pharmaceutical formula showed greater enhancement of quercetin protection against cardiovascular dysfunction associated with metabolic syndrome. In addition, the plain nano-formulation formula (the specific mix of the chosen SNEDDS ingredients; pumpkin seed oil, D-α-tocopheryl polyethylene glycol succinate (TPGS) and PEG 200) itself produced unexpected cardioprotective effect (alone without quercetin). While the suspension of quercetin failed to affect the impaired cardiac contractility in metabolic syndrome animals, the selected nano-pharmaceutical formulation containing the same dose of quercetin completely restored normal cardiac contractility. Thus, the present nano-pharmaceutical formula provides an effective, safe and enhanced protection of cardiovascular complications of the widely speeded metabolic syndrome.

Methods

Experimental Animals

Rats used in this study were male Wistar 6-8 weeks old rats weighing 180-200 g (King Fand Medical Research Center, King Abdulaziz University, Jeddah, Saudi Arabia). Clear polypropylene cages were used to house 4 rats each and included access to purified water and standard rodent pellets. Constant animal housing conditions applied constituting of alternating 12 hours light and dark, a temperature of 22±3° C., a relative humidity of 50-60% and adequate ventilation. Experimental protocol was approved by the Research Ethical Committee, Faculty of Pharmacy, King Abdulaziz University, Jeddah, Saudi Arabia and was conducted in accordance with the Saudi Arabia Research Bioethics and Regulations.

Animals were randomly divided into 5 experimental groups; Control (C) rats received regular tap water and food pellets. MetS group (M) in which fructose (10%) was added to drinking water and NaCl (3%) to food pellets. This regimen began in 6-week old rats and continued for 12 weeks. Standard quercetin group (MQ) administered 25 mg/kg quercetin suspension every day in the last 6 weeks of fructose and salt administration. Nano formula vehicle group (MN) received the same volumes of SNEDDS ingredients (Pumpkin seed oil, D-α-tocopheryl polyethylene glycol succinate (TPGS) and PEG 200) without quercetin every day in the last 6 weeks of fructose and salt administration. The nanoformula group (MNQ) administered 25 mg/kg of quercetin in the form of nano-pharmaceutical formulation every day in the last 6 weeks of fructose and salt administration.

Quercetin Nano Pharmaceutical Formulation

A formula of pumpkin seed oil (PSO), D-α-tocopheryl polyethylene glycol succinate (TPGS) and polyethylene glycol 200 (PEG 200) was used to solubilize quercetin self-nanoemulsifying drug delivery system (SNEDDS). Various ratios of oil, TPGS and PEG 200 were investigated for the formulation of quercetin (Table 1). The loading of quercetin is fixed (25 mg/1 gm formula) and the components of the SNEDDS formula (PSO, TPGS and PEG 200) are added up to 100%.

TABLE 1

| range of SNEDDS formula components. | | | |
| --- | --- | --- | --- |
| SNEDDS components | Units | Low | High |
| oil | % | 0.1 | 0.4 |
| TPGS | % | 0.3 | 0.6 |
| PEG 200 | % | 0.3 | 0.7 |

Quercetin Loaded SNEDDS Globule Size Determination

Globular size for the prepared formulations were analyzed by particle size analyzer (Nano-ZS, Marlvern Instrument, Worcestershire, UK) using a dynamic light scattering technique. 100 μL of each quercetin loaded SNEDDS were diluted with 10 mL of 0.1 N HCL then vortexed for 60 seconds and then analyzed for globule size.

Cardiac Contractility Recording

Invasive real-time recording of cardiac contractility was carried out according to the method described in previous publication from our laboratories (El-Bassossy et al., 2017). After urethane anaethesia, animals were placed on controlled heating pads, and body temperature, measured via a rectal probe, was maintained at 37° C. A microtip pressure transducer (SPR-320; Millar Instruments, Houston, Tex., USA) was inserted into the right carotid artery and advanced into the left ventricle under pressure control. After stabilization for 5 min, the signals were continuously recorded at a sampling rate of 1000 s−1. The microtip catheter was connected to a PowerLab Data Interface Module connected to a PC running LabChart professional software (version 7.3; ADI Instruments, Bella Vista, Australia) containing a blood pressure module.

Cardiac Conductivity Recording

The standard limb lead II of the surface ECG was recorded by the Powerlab system (ADI Instruments) connected to a PC running LabChart professional software (version 7.3) containing an ECG module, which detects different components of the ECG. The change in the ST segment height was used as an index of angina severity (Azhar and El-Bassossy, 2014).

Statistical Analysis

Values are expressed as mean±standard error of the mean. Statistical analysis was carried out by one-way analysis of variance (ANOVA) followed by Newman-Keuls' post hoc test. using Prism 5® software (Graphpad, Calif., USA). Statistical significance was considered when P value <0.05. The sample size was calculated using G*Power 3.1.9.4 free software (Kiel University, Germany) at statistical power value of 0.8 and a value of 0.05.

Results

Quercetin Nano Pharmaceutical Formulation

The prepared formulations of quercetin with varying ratios of SNEDDS components of PSO (oil), TPGS (emulsifier) and PEG 200 (co-surfactant) showed varying globule size according to the ratio of SNEDDS components as indicated in Table 2. The results revealed that at high oil concentration globule size exceeded the nano-range (>1000 nm), while at low oil concentration globule size reduced to <100 nm (F5, Table 2. A formula was selected for in-vivo studies based on globule size of SNEDDS produced.

TABLE 2

| SNEDDS formulations and their observed globule size | | | |
| --- | --- | --- | --- |
| Formula # | PSO | TPGS | PEG200 | Size (nm) |
| F1 | 0.1 | 0.3 | 0.6 | 165.3 |
| F2 | 0.4 | 0.3 | 0.3 | >1000 nm |
| F3 | 0.2 | 0.4 | 0.4 | 362 |
| F4 | 0.1 | 0.5 | 0.4 | 82.6 |
| F5 | 0.2 | 0.5 | 0.3 | 320 |
| F6 | 0.3 | 0.3 | 0.4 | 490 |

Effect on Cardiac Themodynamics

MetS induced by high-fructose high-salt diet feeding for 12 weeks resulted in marked reduction in cardiac contractility as appear from the significant decrease in contractility index compared to control animals (p<0.05, FIG. 1). Daily administration of regular size quercetin (25 mg/kg in the last 6 weeks) did not significantly affect the reduced cardiac contractility in MetS animals. Administration of the plain nano-pharmaceutical formula significantly increased cardiac contractility in MetS but did not completely restore normal cardiac contractility (p<0.05, FIG. 1). However, the quercetin loaded nano-pharmaceutical formula containing the same dose of quercetin completely restored normal cardiac contractility (p<0.05, FIG. 1).

Figure 2A:
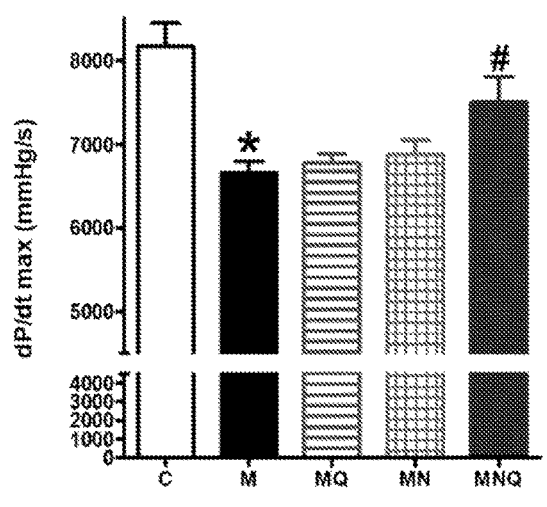
FIG. 2A-B. Effect of oral administration of standard quercetin suspension (MQ), plain nano-pharmaceutical formulation (MN) and the quercetin loaded nano-pharmaceutical formulation (MNQ) both at 25 mg/kg/day on dp/dt max (A) and dp/dt min (B) in metabolic syndrome (M) induced by feeding rats a high fructose (10% in drinking water), high salt (3%) diet for 12 weeks. Results are expressed as mean±SEM (n=8 for all groups). * $p<0.05$ when compared to the corresponding control values, # $p<0.05$ when compared to the corresponding MetS values using one-way ANOVA followed by Dunnet's post-hoc test.
Figure 2B:
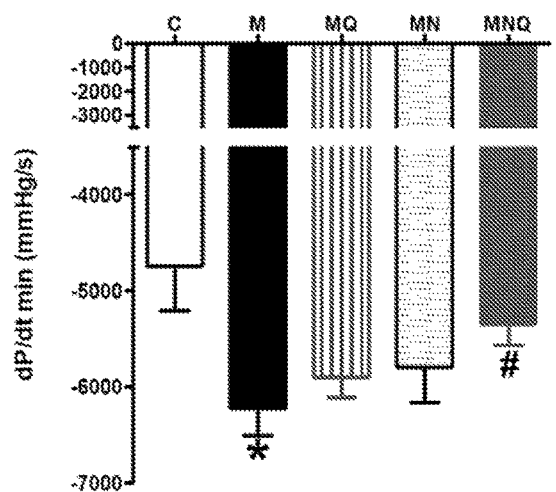

The heart of MetS animals were suffering from both left ventricular systolic dysfunctions, reflected by a significant decrease in dP/dt (p<0.05, FIG. 2A) and diastolic dysfunction, reflected by a significant decrease in −dP/dt (p<0.05, FIG. 2B). The treatment with quercetin or plain nano-pharmaceutical formula did not significantly affect deteriorated cardiac systolic nor diastolic function in MetS animals. However, the quercetin loaded nano-pharmaceutical formula almost restored normal systolic and diastolic cardiac functions (both at p<0.05, FIGS. 2A and 2B).

Effect on Cardiac Conductivity

Figure 3A:
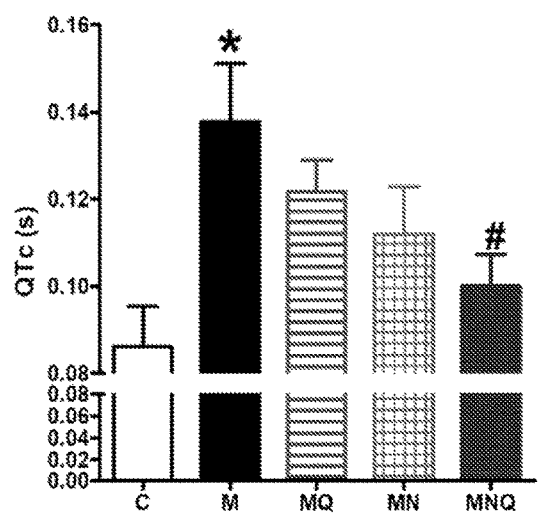
FIG. 3A-B. Effect of oral administration of standard quercetin suspension (MQ), plain nano-pharmaceutical formulation (MN) and the quercetin loaded nano-pharmaceutical formulation (MNQ) both at 25 mg/kg/day on QTc (A) and JT interval (B) in metabolic syndrome (M) induced by feeding rats a high fructose (10% in drinking water), high salt (3%) diet for 12 weeks. Results are expressed as mean±SEM (n=8 for all groups). * $p<0.05$ when compared to the corresponding control values, # $p<0.05$ when compared to the corresponding MetS values using one-way ANOVA followed by Dunnet's post-hoc test.
Figure 3B:
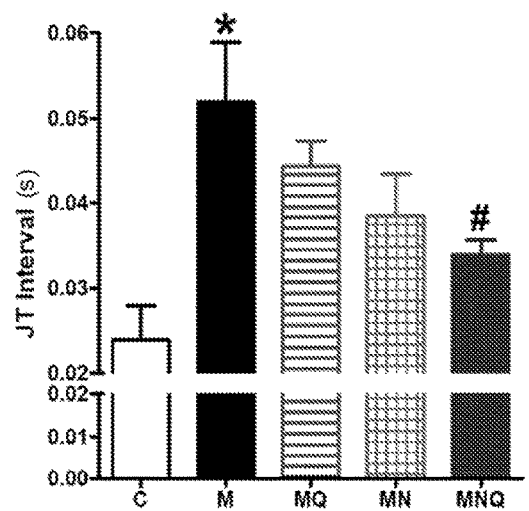

MetS induced by high-fructose high-salt diet resulted in a delayed cardiac repolarization, reflected by a significant prolongation in QTc and JT intervals compared to control values (both at p<0.05, FIG. 3). Quercetin administration did not significantly improve the prolonged QTc, JT intervals in MetS animals. Similarly, the plain nano-pharmaceutical formulation did not produce a statistically significant effect on QTc, JT intervals. However, the nano-pharmaceutical formula of quercetin almost restored normal cardiac repolarization as observed from the significant decrease in QTc, JT intervals (both at p<0.05, FIGS. 3A and 3B).

Effect on Blood Pressure

Figure 4A:
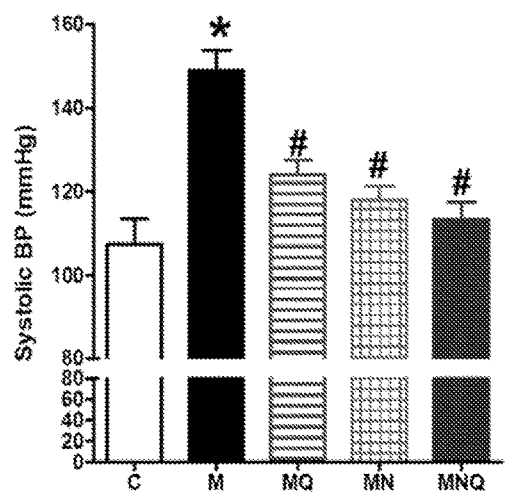
FIG. 4A-B. Effect of oral administration of standard quercetin suspension (MQ), plain nano-pharmaceutical formulation (MN) and the quercetin loaded nano-pharmaceutical formulation (MNQ) both at 25 mg/kg/day on systolic BP (A) and diastolic BP (B) in metabolic syndrome (M) induced by feeding rats a high fructose (10% in drinking water), high salt (3%) diet for 12 weeks. Results are expressed as mean±SEM (n=8 for all groups). * $p<0.05$ when compared to the corresponding control values, # $p<0.05$ when compared to the corresponding MetS values using one-way ANOVA followed by Dunnet's post-hoc test.
Figure 4B:
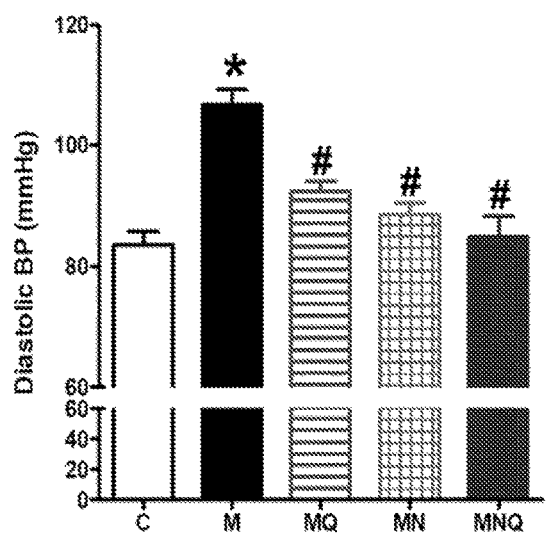

MetS animals showed significant elevation both in systolic (SBP) and diastolic blood pressure (DBP) compared to control animals (both at p<0.05, FIGS. 4A and 4B). Quercetin administration partially reduced the elevations in SBP and DBP compared to MetS animals (both at p<0.05). The plain nano-formula produced similar reductions in SBP and DBP (both at p<0.05). However, the nano-pharmaceutical formula of quercetin vitually abolished the elevations in both systolic and diastolic BP and restored these parameters to nearly control values (both at p<0.05, FIGS. 4A and 4B).

Discussion

The nano-pharmaceutical formula of quercetin consists of safe ingredients forming a nano-emulsion. PSO is a natural oil and TPGS and PEG are approved by the FDA. TPGS, The water-soluble derivative of natural vitamin E, is an amphiphilic excellent solubilizer, emulsifier, permeation and bioavailability enhancer of hydrophobic drugs (Guo et al., 2013; Yang et al., 2018; Zhang et al., 2012). TPGS has a P-glycoprotein (P-gp) inhibition activity that could augment, with solubilizing ability, the efficacy of quercetin (Dintaman and Silverman, 1999).

The current study clearly shows that the current SNEDDS preparation significantly potentiates the quercetin cardiovascular effect. While quercetin administration in the current study failed to completely protect from cardiovascular complication of metabolic syndrome, the current nano-formula containing the same dose of quercetin was able to completely restore normal cardiovascular function.

The enhanced effect of quercetin due to the current nano formulation is not only due to enhanced bioavailability due to SNEDdS formation as the plain nano-formulation (with no quercetin) showed marked cardioprotective effect. This points to a direct effect of the SNEDDDS ingredients, Pumpkin seed oil, D-α-tocopheryl polyethylene glycol succinate (TPGS) and PEG 200), in cardiovascular protection. Pumpkin oil was chosen over other oils in the current SNEDDS preparation because of its anti-inflammatory effect (Fahim et al., 1995) while D-α-tocopheryl polyethylene glycol succinate was chosen based on its antioxidant activities (Engin, 2009). Several reports from our laboratories and others showed key roles of inflammation and oxidative stress in cardiovascular function associated with metabolic syndrome (El-Bassossy et al., 2009; El-Bassossy et al., 2018; El-Bassossy and Watson, 2015).

No previous report has utilized the combination of PSO (oil), TPGS (emulsifier) and PEG 200 (co-surfactant) as a carrier system for the improved delivery and synergistic efficacy of quercetin for protection from cardiovascular complications associated with MetS.

Acknowledgment

This work was supported by the National Science, Technology and Innovation Plan (NSTIP) strategic technologies program in the Kingdom of Saudi Arabia, Project No. 14-BIO929-03. The inventors acknowledge the technical support of Science and Technology unit, King Abdulaziz University.

References

Alberti, K. G. M. M., Zimmet, P., Shaw, J., 2005. The metabolic syndrome—A new worldwide definition. Lancet. https://doi.org/10.1016/S0140-6736(05)67402-8

Azhar, A., El-Bassossy, H. M., 2014. Pentoxifylline alleviates cardiac ischemia and dysfunction following experimental angina in insulin resistance. PLoS One 9. https://doi.org/10.1371/journal.pone.0098281

Bahia, L., Aguiar, L. G., Villela, N., Bottino, D., Godoy-Matos, A. F., Geloneze, B., Tambascia, M., Bouskela, E., Bouskelaa, E., 2006. Relationship between adipokines, inflammation, and vascular reactivity in lean controls and obese subjects with metabolic syndrome. Clinics 61, 433-40. https://doi.org/10.1590/S1807-59322006000500010

Dintaman, J. M., Silverman, J. A., 1999. Inhibition of P-glycoprotein by D-alpha-tocopheryl polyethylene glycol 1000 succinate (TPGS). Pharm. Res. 16, 1550-6.

El-Bassossy, H. M., Banjar, Z. M., El-Mas, M. M., 2017. The inflammatory state provokes sexual dimorphism in left ventricular and electrocardiographic effects of chronic cyclosporine in rats. Sci. Rep. 7. https://doi.org/10.1038/srep42457

Eltobshi, A. A., Mohamed, E. A., Abdelghani, G. M., Nouh, A. T., 2018. Self-nanoemulsifying drug-delivery systems for potentiated anti-inflammatory activity of diacerein. Int. J. Nanomedicine 13, 6585-6602. https://doi.org/10.2147/IJN.S178819

Guo, Y., Luo, J., Tan, S., Otieno, B. O., Zhang, Z., 2013. The applications of Vitamin e TPGS in drug delivery. Eur. J. Pharm. Sci. 49, 175-186. haps://doi.org/10.1016/J.EJPS.2013.02.006

Jagtap, S., Meganathan, K., Wagh, V., Winkler, J., Hescheler, J., Sachinidis, A., 2009. Chemoprotective Mechanism of the Natural Compounds, Epigallocatechin-3-O-Gallate, Quercetin and Curcumin Against Cancer and Cardiovascular Diseases. Curr. Med. Chem. 16, 1451-1462. https://doi.org/10.2174/092986709787909578

Kim, R M, Jang, D. J., Kim, Y. C., Yoon, J. H., MM, K. A., Maeng, H. J., Cho, K. H., 2018. Flurbiprofen-loaded solid SNEDDS preconcentrate for the enhanced solubility, in-vitro dissolution and bioavailability in rats. Pharmaceutics 10. https://doi.org/10.3390/pharmaceutics10040247

Murakami, A., Ashida, H., Terao, J., 2008. Multitargeted cancer prevention by quercetin. Cancer Lett. https://doi.org/10.1016/j.canlet.2008.03.046

Olijhoek, J. K., Van Der Graaf, Y., Banga, J.-D. D., Algra, A., Rabelink, T. J., Visseren, F. L. J. J., SMART Study Group, 2004. The Metabolic Syndrome is associated with advanced vascular damage in patients with coronary heart disease, stroke, peripheral arterial disease or abdominal aortic aneurysm. Eur. Heart J. 25, 342-348. https://doi.org/10.1016/j.ehj.2003.12.007

Oliver, J. J., Webb, D. J., 2003. Noninvasive assessment of arterial stiffness and risk of atherosclerotic events. Arterioscler. Thromb. Vasc. Biol. 23, 554-566. https://doi.org/10.1161/01. ATV.0000060460.52916. D6

Shen, Y., Croft, K. D., Hodgson, J. M., Kyle, R., Lee, I. L. E., Wang, Y., Stocker, R., Ward, N.C., 2012. Quercetin and its metabolites improve vessel function by inducing eNOS activity via phosphorylation of AMPK. Biochem. Pharmacol. 84, 1036-1044. https://doi.org/10.1016/j.bcp.2012.07.016

Valicherla, G. R., Dave, K. M., Syed, A. A., Riyazuddin, M., Gupta, A. P., Singh, A., Wahajuddin, Mitra, K., Datta, D., Gayen, J. R., 2016. Formulation optimization of Docetaxel loaded self-emulsifying drug delivery system to enhance bioavailability and anti-tumor activity. Sci. Rep. 6. https://doi.org/10.1038/srep26895

Visioli, F., 2011. Nutritional support in the pharmacological treatment of metabolic syndrome. Eur. J. Pharmacol. 668, S43-S49. https://doi.org/10.1016/j.ejphar.2011.05.083

Yang, C., Wu, T., Qi, Y., Zhang, Z., 2018. Recent Advances in the Application of Vitamin E TPGS for Drug Delivery. Theranostics 8, 464-485. https://doi.org/10.7150/thno.22711

Zhang, Z., Tan, S., Feng, S. S. S. S., 2012. Vitamin E TPGS as a molecular biomaterial for drug delivery. Biomaterials 33, 4889-4906. https://doi.org/10.1016/j.biomaterials.2012.03.046

Bardaa, S., Ben Halima, N., Aloui, F., Ben Mansour, R., Jabeur, H., Bouaziz, M., Sahnoun, Z., 2016. Oil from pumpkin (*Cucurbita pepo* L.) seeds: evaluation of its functional properties on wound healing in rats. Lipids Health Dis 15, 73.

Caili, F., Huan, S., Quanhong, L., 2006. A review on pharmacological activities and utilization technologies of pumpkin. Plant Foods Hum Nutr 61, 73-80.

Carini, R., Poli, G., Dianzani, M. U., Maddix, S. P., Slater, T. F., Cheeseman, K. H., 1990. Comparative evaluation of the antioxidant activity of alpha-tocopherol, alpha-tocopherol polyethylene glycol 1000 succinate and alpha-tocopherol succinate in isolated hepatocytes and liver microsomal suspensions. Biochem Pharmacol 39, 1597-1601.

Collnot, E. M., Baldes, C., Wempe, M. F., Hyatt, J., Navarro, L., Edgar, K. J., Schaefer, U. F., Lehr, C. M., 2006. Influence of vitamin E TPGS poly(ethylene glycol) chain length on apical efflux transporters in Caco-2 cell monolayers. J Control Release 111, 35-40.

Constantinides, P. P., Han, J., Davis, S. S., 2006. Advances in the use of tocols as drug delivery vehicles. Pharm Res 23, 243-255.

Dintaman, J. M., Silverman, J. A., 1999. Inhibition of P-glycoprotein by D-alpha-tocopheryl polyethylene glycol 1000 succinate (TPGS). Pharm Res 16, 1550-1556.

El-Bassossy, H. M., El-Maraghy, N. N., El-Fayoumi, H. M., Watson, M. L., 2009. Haem oxygenase-1 induction protects against tumour necrosis factor alpha impairment of endothelial-dependent relaxation in rat isolated pulmonary artery. Br J Pharmacol 158, 1527-1535.

El-Bassossy, H. M., Neamatallah, T., Balamash, K. S., Abushareb, A. T., Watson, M. L., 2018. Arginase overexpression and NADPH oxidase stimulation underlie impaired vasodilation induced by advanced glycation end products. Biochem Biophys Res Commun 499, 992-997.

El-Bassossy, H. M., Watson, M. L., 2015. Xanthine oxidase inhibition alleviates the cardiac complications of insulin resistance: effect on low grade inflammation and the angiotensin system. J Transl Med 13, 82.

Engin, K. N., 2009. Alpha-tocopherol: looking beyond an antioxidant. Mol Vis 15, 855-860.

Fahim, A. T., Abd-el Fattah, A. A., Agha, A. M., Gad, M. Z., 1995. Effect of pumpkin-seed oil on the level of free radical scavengers induced during adjuvant-arthritis in rats. Pharmacol Res 31, 73-79.

Farzaei, M. H., Shams-Ardekani, M. R., Abbasabadi, Z., Rahimi, R., 2013. Scientific evaluation of edible fruits and spices used for the treatment of peptic ulcer in traditional Iranian medicine. ISRN Gastroenterol 2013, 136932.

Guo, Y., Luo, J., Tan, S., Otieno, B. O., Zhang, Z., 2013. The applications of Vitamin E TPGS in drug delivery. Eur J Pharm Sci 49, 175-186.

Sadoqi, M., Lau-Cam, C. A., Wu, S. H., 2009. Investigation of the micellar properties of the tocopheryl polyethylene glycol succinate surfactants TPGS 400 and TPGS 1000 by steady state fluorometry. J Colloid Interface Sci 333, 585-589.

Stevenson, D. G., Eller, F. J., Wang, L., Jane, J. L., Wang, T., Inglett, G. E., 2007. Oil and tocopherol content and composition of pumpkin seed oil in 12 cultivars. J Agric Food Chem 55, 4005-4013.

Varma, M. V., Panchagnula, R., 2005 Enhanced oral paclitaxel absorption with vitamin E-TPGS: effect on solubility and permeability in vitro, in situ and in vivo. Eur J Pharm Sci 25, 445-453.

Yu, L., Bridgers, A., Polli, J., Vickers, A., Long, S., Roy, A., Winnike, R., Coffin, M., 1999. Vitamin E-TPGS increases absorption flux of an HIV protease inhibitor by enhancing its solubility and permeability. Pharm Res 16, 1812-1817.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A cardiac treatment nano-emulsion formulation, comprising a therapeutically effective amount of pumpkin seed oil;
   D-α-tocopheryl polyethylene glycol succinate (TPGS);
   polyethylene glycol (PEG) 200; and
   quercetin at a dosage of 1-30 mg/kg,
   wherein TPGS and PEG 200 are present in an amount sufficient to form a nano-emulsion.

2. The formulation of claim 1, wherein the concentration of pumpkin seed oil is 20%.

3. The formulation of claim 1, wherein the concentration of TPGS is 50%.

4. The formulation of claim 1, wherein the concentration of PEG 200 is 30%.

5. A cardiac treatment formulation, comprising:
   pumpkin seed oil at a concentration of 10-40%;
   D-α-tocopheryl polyethylene glycol succinate (TPGS) at a concentration of 30-70%;
   polyethylene glycol (PEG) 200 at a concentration of 30-60%; and
   quercetin at a dosage of 1-30 mg/kg.

* * * * *